US008137257B1

(12) United States Patent
Berdut Teruel

(10) Patent No.: US 8,137,257 B1
(45) Date of Patent: Mar. 20, 2012

(54) MAGNETIC THERAPEUTIC DEVICE AND METHOD OF USING THE SAME

(76) Inventor: Elberto Berdut Teruel, San Juan, PR (US)

( * ) Notice: Subject to any disclaimer, the term of this patent is extended or adjusted under 35 U.S.C. 154(b) by 0 days.

(21) Appl. No.: 12/974,015

(22) Filed: Dec. 21, 2010

Related U.S. Application Data

(63) Continuation-in-part of application No. 11/248,067, filed on Oct. 12, 2005, now abandoned.

(51) Int. Cl.
*A61N 2/00* (2006.01)
(52) U.S. Cl. .......................................................... 600/9
(58) Field of Classification Search ................. 600/9–15
See application file for complete search history.

(56) References Cited

U.S. PATENT DOCUMENTS

| 435,343 | A | * | 8/1890 | Brown | 600/13 |
| 1,001,236 | A | * | 8/1911 | Bachelet | 600/13 |
| 3,658,051 | A | * | 4/1972 | MacLean | 600/14 |
| 5,642,739 | A | * | 7/1997 | Fareed | 128/881 |
| 2007/0038015 | A1 | * | 2/2007 | Quail | 600/9 |

* cited by examiner

*Primary Examiner* — John Lacyk
(74) *Attorney, Agent, or Firm* — Luis Figarella

(57) ABSTRACT

A magnetic therapeutic device useful for medical purposes wherein the head or body part of a user is exposed to a magnetic field created by magnetic elements having opposite polarities. One side of the treated volume, member or body cavity receives a magnetic flux having a north to south polarity while at the same time the opposite side of the treated volume or member is subject to a south to north polarity. The magnetic therapeutic device comprises two permanently mounted magnetic elements, means for mounting the said magnetic elements and means for holding the said magnetic elements at a particular location and substantially opposite sides to each other.

5 Claims, 4 Drawing Sheets

MAGNETIC THERAPEUTIC DEVICE AND METHOD OF USING THE SAME

CROSS-REFERENCE TO RELATED APPLICATIONS

This application is a continuation-in-part of pending U.S. Appl. "Magnetic Therapeutic Device and Method of Using the Same", Ser. No. 11/248,067, filed on Oct. 12, 2005 the disclosure of which is incorporated herein by reference in its entirety.

TECHNICAL FIELD

This invention relates to a magnetic therapeutic device useful for therapeutic purposes. More particularly, this invention relates to a head magnetic device and a process to treat and or prevent migraine, body pain, sleeplessness, menstrual pain, depression and other stress related conditions or diseases comprising the said magnetic therapeutic device.

BACKGROUND

The prior art discloses many inventions wherein a variety of devices or items containing magnets are described and recommended for treating, preventing or improving diverse health conditions.

Treskov et al, U.S. Pat. No. 6,332,469 discloses a body part shaving item comprising magnets in order to reduce the skin irritation, promoting faster healing of skin cuts and having a prophylactic and healing effect on the body part subjected to shaving. Yang, U.S. Pat. No. 5,891,331 discloses a portable magnetic device similar to a fountain pen and useful in purifying water and other drinks by exposing the said liquids to bio ceramics and magnets. The said magnetized liquids are said to promote blood circulation as well as to improve digestion and absorption.

Shimiyashu, U.S. Pat. No. 4,480,596; Smith et al, U.S. Pat. No. 6,623,419 as well as Martello U.S. Pat. No. 6,551,234 and Getek, U.S. Pat. No. 6,406,418 are examples of US Patents wherein therapeutic magnetic belts are used in order to reduce musculoskeletal pain, counteract fat and or reducing muscles stiffness by exposing the described body areas to magnetic flux.

Roberts et al U.S. Pat. No. 6,632,168 discloses a magnetic therapeutic device and a method to treat pain or injury areas comprising the use of the said magnetic device under the wearer's skin. Steponovich, U.S. Pat. No. 6,610,023 discloses a strap having magnets that is conveniently wrapped around the knee, giving support to the knee joint that allows the wearer to have maximum knee activity while helping him or her to overcome pain and diseases associated with the knee.

Many everyday use articles such as pads, adhesive bands, patches, bandages and wrapping materials comprising magnetic items and directed to the magnetotherapy of different parts of the body are disclosed in multiple US Patents. So do Juster et al, U.S. Pat. No. 6,344,021, Engel U.S. Pat. No. 6,146,324, Nagler U.S. Pat. No. 6,093,143, Snider U.S. Pat. No. 5,336,498, Russell U.S. Pat. No. 5,782,743 and Griffin et al U.S. Pat. No. 4,587,956 among others.

Furthermore, magnetic body ornaments and/or jewelry, such as rings, bracelets, necklaces, chain belts, earrings and wrist watches have been already disclosed in patented publications, such as Chiu U.S. Pat. No. 5,989,178, Ishikawa U.S. Pat. No. 4,095,587, Monden et al U.S. Pat. No. 4,186,567 and Li et al U.S. Pat. No. 5,226,020, among others. The said items are said to promote health conditions in the wearer and in many instances preventing the wearer of getting ill.

The prior art also discloses other multiple magnetic items such as shoes, pillows and gloves that are intended to promote health via exposing the body to the magnetic flux integrated in the said items, see for instance, Qui et al U.S. Pat. No. 6,151,807, Greenwalt U.S. Patent No. 5,976,100, Komuro U.S. Pat. No. 5,193,236 and Chen U.S. Pat. No. 6,085,355, among others.

Interestingly, some magneto-therapeutic devices are designed to treat particular medical conditions, for instance, Haglund U.S. Pat. No. 6,053,859 discloses a magnetic apparatus and method comprising the same in the treatment of sinus conditions. Paturu U.S. Patent Application publication 20020151759 discloses a method for treatment of erectile dysfunction, peripheral vascular disease, cerebral insufficiency and certain vascular pathologies. Ross U.S. Pat. No. 5,718,721 and Fichell et al U.S. Pat. No. 6,402,678 disclose methods for the treating of migraine headache pain by exposing selective parts of the body to magnetic flux.

Wascher et al U.S. Pat. No. 6,443,882 and Bouldin et al U.S. Pat. No. 6,149,577 disclose an apparatus and method comprising the said magneto therapeutic device in the treatment of degenerative diseases and disorders. The full contents of the above cited references are herein incorporated by reference in their entirety.

In general terms, the prior art recognizes that the magneto therapy functions in the treatment of multiple medical diseases and/or conditions by increasing the blood circulation and energizing a particular part of the body once it is exposed to the magnetic energy or flux of magnets. Increasing blood's circulation helps to oxygenate the vital organs and tissues and help to clear up veins and arteries, stimulating the body to promote its healing function naturally.

There is a need for new methods of using magneto therapeutic devices in treating medical conditions and/or diseases such as migraine, muscle pain, sleeplessness, menstrual pain, stress related conditions and/or diseases, wherein the said method is a noninvasive technique that does not requires the use of medical compositions and lacks any risks of pernicious secondary effects.

SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

In one aspect, the invention comprises a magnetic therapeutic apparatus comprising an arcuate main body comprised of two permanent magnet mounting locations separated by a gap, wherein said main body is made of a durable, flexible and adjustable material capable of keeping the permanent magnet mounting locations substantially aligned to each other, a first permanent magnet magnetic element positioned on the first magnet mounting station with a magnetic polarity North to South, wherein said first magnetic element is permanently mounted so that its South polarity side is fixed in place and facing the inside of the cavity formed by the main body, a second permanent magnet magnetic element positioned on the second mounting station magnetic polarity South to North, wherein said second magnetic element is permanently mechanically mounted so that its North polarity side is fixed in place and facing the inside of the cavity formed by the curved main body; and the cavity formed by the main body has a gap in its perimeter.

In another aspect the magnetic elements are selected from a group consisting of rare earth, neodymium, ceramic materials or mixtures thereof. In yet another aspect, the magnetic elements are neodymium magnets or ceramic magnets. In yet another aspect of the invention, the magnetic elements have a cylinder, annular; hexagonal, octagonal or square form.

In another aspect of the invention, the invention comprises a magnetic therapeutic apparatus comprising an arcuate main body comprised of two permanent magnet assemblies separated by a gap, wherein said main body is made of a durable, flexible and adjustable material capable of keeping the permanent magnet mounting locations substantially aligned to each other; each of said assemblies is made up of a rim with an opening through which a leg of the arcuate structure is inserted, said leg having a protrusion at its end, which is sandwiched between a permanent magnetic element with a specific polarity facing one side, and a ferrous metal disk on the other, a first permanent magnetic assembly element positioned on one side of the arcuate structure with a magnetic polarity North to South, wherein said first magnetic assembly is permanently mounted so that its South polarity side is fixed in place and facing the inside of the cavity formed by the arcuate main body, a second permanent magnetic assembly element positioned on the other one side of the arcuate structure with a magnetic polarity South to North, wherein said second magnetic assembly is permanently mechanically mounted so that its North polarity side is fixed in place and facing the inside of the cavity formed by the curved main body; and the cavity formed by the main body has a gap in its perimeter.

In another aspect, the magnetic elements are selected from a group consisting of rare earth, neodymium, ceramic materials or mixtures thereof. In one aspect the magnetic elements are neodymium magnets or ceramic magnets. In yet another aspect, the magnetic elements have a cylinder, annular; hexagonal, octagonal or square form.

Other features and advantages of the present invention will become apparent upon examining the following detailed description of an embodiment thereof, taken in conjunction with the attached drawings.

DETAILED DESCRIPTION

To provide an overall understanding of the invention, certain illustrative embodiments will now be described, including apparatus and methods. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope hereof.

Figure 1:
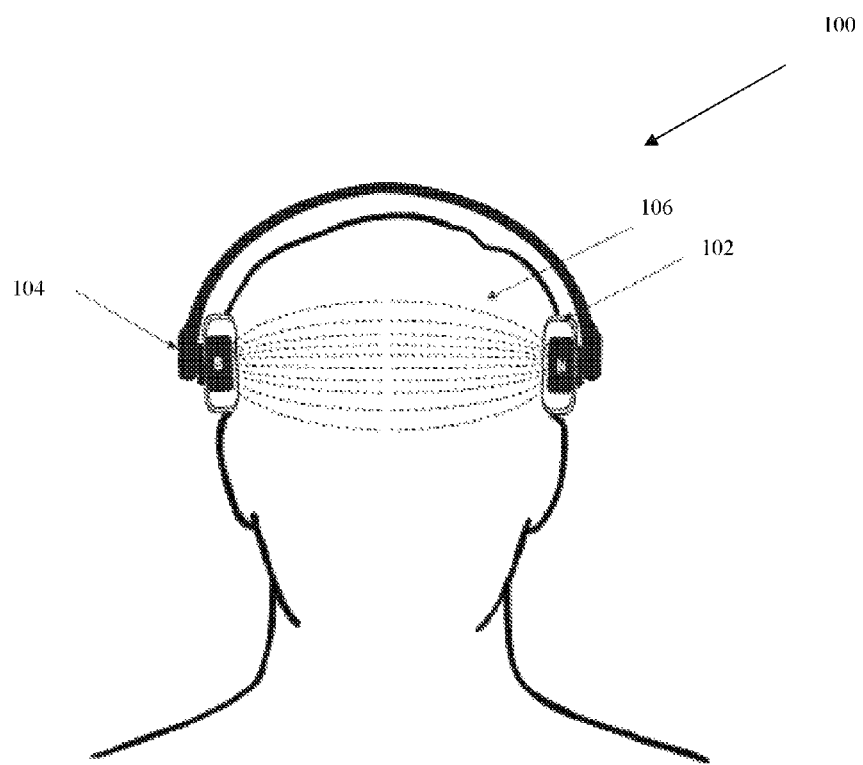
FIG. 1 shows an illustration of a user wearing a device across their temples according to an exemplary embodiment of the invention.

In one embodiment, the magnetic therapeutic device 100 comprises two permanent magnet elements 102 and 104, with each one designed to be positioned in a substantially aligned position across a person's body part. In one embodiment, this is accomplished by the permanent placement of the magnet elements 102, 104 across the user's or wearer's head as illustrated in FIG. 1. Notice that in one embodiment, the magnetic elements are oriented in such a way that one of them has a polarity directed south to north 104, while the other has its polarity oriented in the opposite way, north to south 102. Through this arrangement, the magnetic flux 106 emitted by the magnets is directed across the head or muscle space from one element 102 to the other 104 are opposite to each other.

Regardless of the relative position—left or right—in the wearer's head, the magnetic elements 102 and 104 should be oriented with an opposite polarity relative to each other. In another words, one of the magnetic element's polarity should be oriented south to north while it's counterpart across the body part being treated should be oriented north to south irrespectively of the head side—left or right—wherein anyone of the particular magnetic elements is located.

Figure 2:
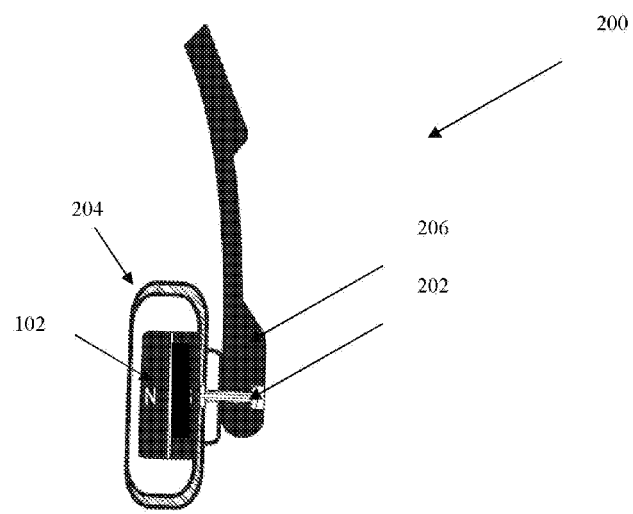
FIG. 2 shows an illustration of a permanently mounted magnet on one side of the arc according to an exemplary embodiment of the invention.

FIG. 2 illustrates a close up 200 of the permanent magnet element 102 from one side of the assembly. The permanent magnetic element is permanently attached through mechanical or chemical means. In one embodiment, this is done through the placing of a rivet 202 through both all or portions of the permanent element 102 housing 204 and all or portions significantly at the end of the arcuate structure 200 holding the elements 102, 104. In an alternate embodiment, the magnetic elements and/or their housings are chemically attached to the arcuate structure 200.

Figure 3:
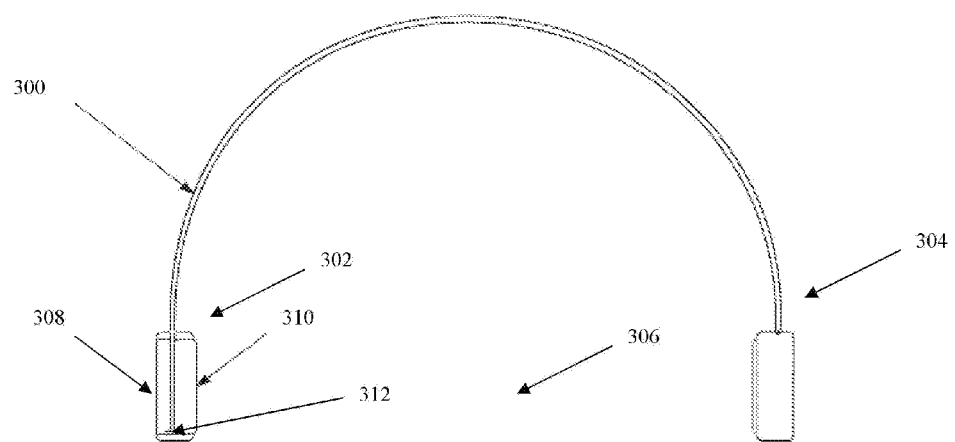
FIGS. 3, 4 and 5 show illustrations of a permanent magnet headset and construction details, according to an exemplary embodiment of the invention.
Figure 4:
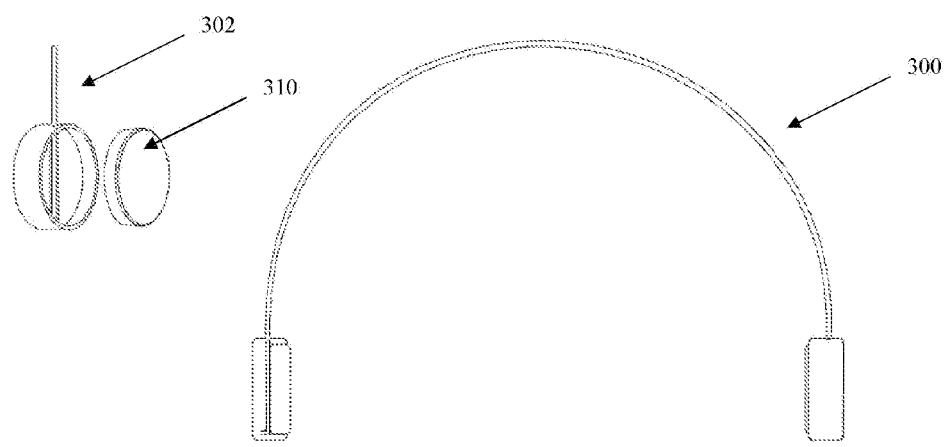
Figure 5:
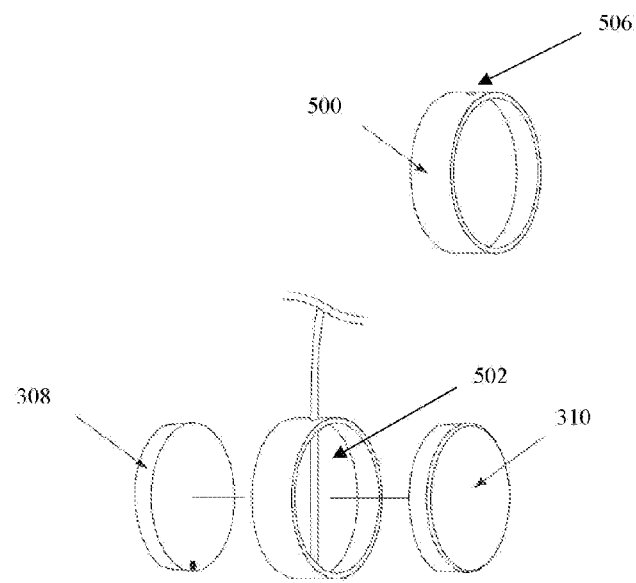

In an alternate embodiment, exemplary illustrated in FIGS. 3, 4 and 5, the assembly is created as an arcuate structure 300 holding the permanent magnet element within assemblies 302, 304 significantly placed near the extremes of the arc. In one embodiment, this assembly creates a headset assembly, uniquely suited to be placed on the head so that the magnets exact location on each side of their temple may be adjusted by the user. The arcuate body shape 300 leaves a gap 306 between the magnetic assemblies 302, 304.

The permanent magnet element assemblies 302, 304 are comprised of a composite assembly on each side. Each assembly is comprised of a rim or ring 500 having at least one opening 506 though which a leg 502 of the arcuate structure is threaded. In one embodiment, the end of the leg 502 is given a knob, bulge, protuberance, flattening or protrusion 312 so that the end of the leg 502 may be trapped between the sandwich of a permanent magnet element 310 and a ferrous metal disk 308. In an alternate embodiment, chemical means (e.g. glue, cement, or other chemical fixation means) or mechanical means (e.g. welding, etc.) are used to securely accomplish the assemblies (302, 304).

Figure 6:
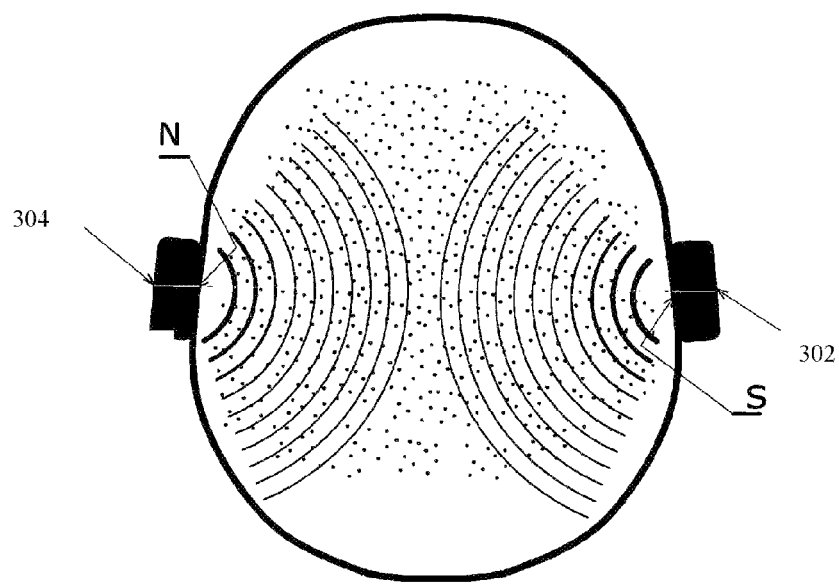
FIGS. 6 and 7 show illustrations of the magnetic field when the magnets are positioned on each side of the user's temples from a top view and front view perspective respectively, according to an exemplary embodiment of the invention.
Figure 7:
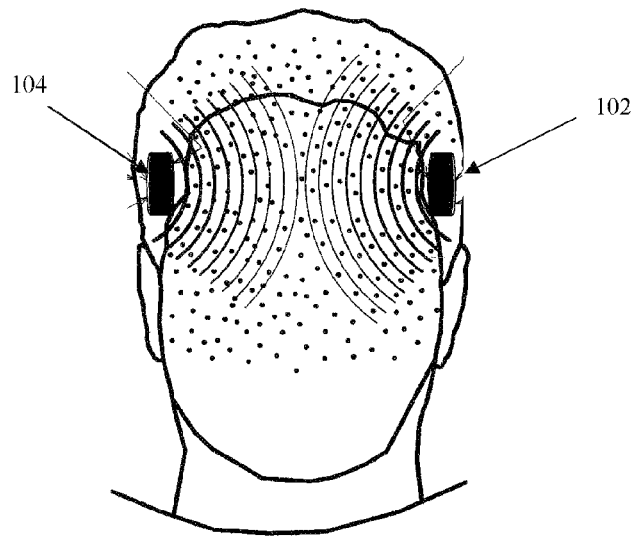

FIGS. 6 and 7 illustrate the effect of the magnets when placed across the cranial cavity. In one embodiment, the magnetic elements 102, 104 or 302, 304 are placed substantially in the region between the forehead bone and the ears. It should be noted that the means to hold or mount the magnetic elements while important, since it provides the proper fixing and stability to place the magnet elements 102, 104 or 302, 304, are not essential to the device's functioning. Therefore, said magnetic elements may be mounted and or held by any conventional means for mounting or holding different elements to be wore around the head area, as long as the proper fixing and stability are provided by the selected means.

In addition to the arcuate embodiments shown above, the magnetic elements may be permanently placed in caps, hats, headsets, construction helmets and others. They may be also incorporated in belts, wherein the magnetic elements are mounted and may be tightened up to the convenience of the wearer in such way that the proper fixing and tightness required is achieved. In an alternate embodiment, said magnetic elements may be inserted in lateral pockets of a hat.

The permanent magnets comprising the magnetic elements 102, 104 or 302, 304 may contain variable magnetic strength and shapes. The term magnetic element herein used is intended to describe the part of the device containing one or more magnets. If more than one magnet is used in a given magnetic element, they may be placed in a stacked configuration. The phrase stacked configurations is intended to mean herein that a magnet is magnetically placed over the top of the other successively, thus each stack of magnets forming what is herein called a magnetic element unit.

Optionally, magnets may also be glued to one another even when they are magnetically attractive to each other. In case of the embodiment wherein the plate is used, a magnet may be placed at the bottom surface of the said plate while one or more can be placed on the top surface. Whenever the said plate is not magnetically attractive to the magnets placed over it, they may be glued to the said surface.

The magnets herein disclosed may be formed from any suitable magnetic material, preferably from rare earth, neodymium, ceramic or mixture thereof. The intensity of the magnetic force of the magnets may be varied and easily increased or decreased by the user by simply adding or subtracting magnets from the device at the wearer's convenience.

The device described herein may be used in the treatment of headache, migraine, pain insomnia and stressfulness related conditions or in the prevention or prophylactic measure of the said conditions. Said prevention or treatment may be achieved by placing the magnetic elements to the head so that the magnetic elements are positioned in the sides of the head substantially located between the forehead and the ears as illustrated in FIGS. 6 and 7. Alternatively, they may be placed in nearby areas.

Various embodiments and features of the present invention have been described in detail with a certain degree of particularity. The utilities thereof can be appreciated by those skilled in the art. It should be emphasized that the above-described embodiments of the present invention merely describe possible examples of the implementations to set forth a clear understanding of the principles of the invention, and that numerous changes, variations, and modifications can be made to the embodiments described herein without departing from the spirit and scope of principles of the invention. Also, such variations and modifications are intended to be included herein within the scope of the present invention, as set forth in the appended claims. The scope of the present invention is defined by the appended claims, rather than the forgoing description of embodiments. Accordingly, what is desired to be secured by Letters Patent is the invention as defined and differentiated in the following claims, and all equivalents.

The invention claimed is:

1. A magnetic therapeutic apparatus comprising;
an arcuate main body comprised of two permanent magnet assemblies separated by a gap, wherein said main body is made of a flexible material capable of keeping the first permanent magnet mounting location substantially aligned to the second permanent magnet mounting location;
said first and said second permanent magnet assemblies are each made up of a rim with an opening through which a leg of the arcuate structure is inserted, said leg having a protrusion at its end, which is sandwiched between a permanent magnetic element with a specific polarity facing one side, and a ferrous metal disk on the other;
said first permanent magnetic assembly element is positioned on one side of the arcuate structure with a magnetic polarity North to South, wherein said first magnetic assembly is permanently mounted so that its South polarity side is fixed in place and facing the inside of the cavity formed by the arcuate main body;
said second permanent magnetic assembly element is positioned on the other one side of the arcuate structure with a magnetic polarity South to North, wherein said second magnetic assembly is permanently mechanically mounted so that its North polarity side is fixed in place and facing the inside of the cavity formed by the curved main body; and
the cavity formed by the main body has a gap in its perimeter.

2. The magnetic therapeutic apparatus of claim 1, wherein the magnetic elements are selected from a group consisting of rare earth, neodymium, ceramic materials or mixtures thereof.

3. The magnetic therapeutic apparatus of claim 1, wherein the magnetic elements are neodymium magnets.

4. The magnetic therapeutic apparatus of claim 1, wherein the magnetic elements are ceramic magnets.

5. The magnetic therapeutic apparatus of claim 1, wherein the magnetic elements have a cylinder, annular; hexagonal, octagonal or square form.

\* \* \* \* \*